United States Patent [19]

Charbonneau

[11] Patent Number: 5,500,208
[45] Date of Patent: Mar. 19, 1996

[54] ORAL COMPOSITIONS COMPRISING A NOVEL TRIPEPTIDE

[75] Inventor: Duane L. Charbonneau, Middletown, Ohio

[73] Assignee: The Procter & Gamble Company, Cincinnati, Ohio

[21] Appl. No.: 255,021

[22] Filed: Jun. 7, 1994

[51] Int. Cl.$^6$ ..................................................... A61K 7/24
[52] U.S. Cl. ............................. 424/55; 562/561; 562/575
[58] Field of Search .............................. 424/55; 562/561, 562/575

[56] References Cited

U.S. PATENT DOCUMENTS

| 4,866,161 | 9/1989 | Sikes et al. | 531/324 |
| 5,171,561 | 12/1992 | Nathoo et al. | 424/53 |

FOREIGN PATENT DOCUMENTS

| 92/06191 | 4/1992 | WIPO | A61K 37/64 |

OTHER PUBLICATIONS

CA 84:12741 1975.
CA 98:157700 1982.
Lamberts, B. L., E. D. Pederson and L. G. Simonson, "The Effects of Basic and Acidic Synthetic Polypeptides on the adherence of the Oral Bacterial, *Streptococcus mutans* and *Streptococcus sanguis*, to Hydroxyapatite", *Archs. Oral Biol.*, vol. 30, No. 3 (1985), pp. 295–298.

*Primary Examiner*—Paul J. Killos
*Attorney, Agent, or Firm*—Betty J. Zea; Karen F. Clark; Jacobus C. Rasser

[57] ABSTRACT

The present invention relates to a tripepride having the amino acid sequence Alanine-Isoleucine-Phenylalanine. This invention also relates to methods and compositions for inhibiting growth of dental plaque on tissues within an oral cavity of a human or other animal comprising topical administration, to tissues of such oral cavity, of a composition comprising a safe and effective amount of the tripepride.

23 Claims, No Drawings

ORAL COMPOSITIONS COMPRISING A NOVEL TRIPEPTIDE

TECHNICAL FIELD

The present invention relates to oral compositions, such as dentifrices and oral solutions, designed to inhibit or prevent the growth of dental plaque on tissues within the oral cavity of a human or other animal.

BACKGROUND OF THE INVENTION

The mouth is a habitat for microbial growth and colonization. Oral cavity surfaces, including the gums, cheek, tongue and teeth provide surfaces for the colonization and accumulation of bacteria. Teeth are unique in the oral cavity because they have hard, non-shedding surfaces where bacteria and dental plaque can significantly accumulate, especially in approximal areas and along the gingival crevice.

Dental plaque is a rough sticky film on the teeth that is made up of saliva, bacteria and food particles which adheres tenaciously to teeth at points of irregularity or discontinuity. Within a few hours of teeth cleaning, a film of salivary proteins, forms on the teeth. Various oral bacteria colonize and multiply, forming a layer of plaque.

The oral bacteria in dental plaque includes many gram positive and gram negative microorganisms embedded in an extracellular matrix of insoluble polysaccharides, firmly attached to teeth and other oral surfaces. The colonization of bacteria to form dental plaque follows an ecological pattern where a few pioneer species, mostly gram-positive streptococci, colonize enamel surfaces. The plaque then progresses through stages of increasing microbial complexity. Mature plaques, often found in protected regions of the teeth, such as cracks, approximal regions and in the gingival crevice, typically contain anaerobes. Saliva and crevicular fluid are a source of nutrients for the dental plaque. Local conditions affect the metabolic activity and composition of dental plaque.

If not prevented or removed, plaque may become embedded with mineral salts, containing calcium and phosphate, to form a hard crusty deposit, calculus or tartar, on the teeth. Calculus may be white or yellowish in color or may be stained or discolored by extraneous agents. Calculus tends to be more unsightly than plaque and much more difficult to remove from the teeth. The toxins in plaque and calculus can irritate the gingival tissues surrounding the coated teeth, causing inflammation and destruction of the gums which can lead to other complications.

Applicant has unexpectedly found that the tripeptide, Alanine-Isoleucine-Valine (Ala-Ile-Val), applied to oral cavity tissues inhibits the accumulation of plaque on the tissues. Applicant has also unexpectedly found that Ala-Ile-Val in combination with the tripeptide, Serine-LeucinePhenylalanine, also inhibits the accumulation of plaque on oral cavity surfaces and that this antiplaque benefit is enhanced relative to Ala-Ile-Val applied alone.

SUMMARY OF THE INVENTION

The present invention relates to a tripeptide having the amino acid sequence Alanine-lsoleucine-Valine. This invention also relates to methods and compositions for inhibiting growth of dental plaque on tissues within an oral cavity of a human or other animal comprising topical administration, to tissues of such oral cavity, of a composition comprising a safe and effective amount of the tripeptide.

DETAILED DISCLOSURE OF THE INVENTION

The present invention relates to active agents, methods and compositions for inhibiting the adherence of oral bacteria to surfaces within the oral cavity of humans or other animals comprising administration of a composition comprising a tripepride having the sequence:

Alanine-lsoleucine-Valine to the surfaces within the oral cavity.

One aspect of the present invention is the tripeptide itself. The peptide Alanylisoleucinylvaline (AIV)is synthesized using FastMoc® chemistry (Applied Biosystems, Foster City, Calif.) on an ABI 430 A peptide synthesizer (Applied Biosystems). FluorenylmethoxycabonyI-Valine-p-Benzyloxybenzyl Alcohol resin, (Fmoc-Val-Wang resin), purchased from Advanced ChemTech (Louisville, Ky.) is used as the starting material. The peptide is synthesized utilizing the FastMoc® cycles, which include deprotection of the amino terminal Fmoc group with piperidine (Aldrich Chemical, Milwaukee, Wis.), 25% in N-methylpyrrollidinone (NMP) (J. T. Baker, Philipsburg, N.J.) and coupling of the next Fmoc-amino acid residue via activation of the carboxyl group with 0.45 M H-Benzotriazole-N,N,N',N'-Tetramethyluronium-hexafluorophosphate (HBTU) (Applied Biosystems).

The peptide is cleaved from the resin by adding 9.5 ml Trifluroacetic acid (TFA), 0.5 ml $H_2O$ to the peptidyl resin in a stoppered round bottom and allowed to stir for 1.5 hours at room temperature. The solution is then filtered through a medium porosity glass frit and the filtrate reduced in volume to 2 ml in vacuo. The solution is then diluted with 20 ml of $H_2O$ and washed three times with 20 ml of ether. The aqueous layer is lyophilized overnight.

The crude peptide is characterized using Ion Spray Mass Spectrometry (Sciex) and by reversed phase-high pressure liquid chromatography (RP-HPLC) using a Beckman HPLC system, 167 Detector, 126 Pumps (Beckman, Palo Alto, Calif.) with a gradient of 0%-40% $CH_3CN$ (0.1% TFA) over 40 min. on a Vydac (The Nest Group, Southborough, Mass.) column (4.6×250 mm, 5 μm 300Å) at a flow rate of 1 ml $min^{-1}$.

The crude peptide is then preparatively purified using RP-HPLC with the above conditions on a Vydac column (22×250 mm, 10 μm 300Å) at a flow rate of 10 ml $min^{-1}$.

By "safe and effective amount" as used herein is meant an amount of compound or composition sufficient to induce a significant positive modification in the condition to be treated, but low enough to avoid serious side effects (at a reasonable benefit/risk ratio), within the scope of sound medical judgment. The safe and effective amount of the compound or composition will vary with the particular condition being treated, the age and physical condition of the patient being treated, the severity of the condition, the duration of the treatment, the nature of concurrent therapy, the specific compound or composition employed, the particular pharmaceutically-acceptable carrier utilized, and like factors.

By the term "comprising", as used herein, is meant that various additional components can be conjointly employed in the compositions of this invention.

The compositions of the present invention, compositions of the present invention comprise a safe and effective amount of Ala-Ile-Val, preferably from about 0.001% to about 10%, more preferably from about 0.01% to about 5%, more preferably still from about 0.1% to about 3%, still more preferably from about 0.1% to about 2% of Ala-Ile-Val by weight of the composition. For a mouth rinse or other pharmaceutically-acceptable liquid formulation, the most preferred concentration of Ala-Ile-Val ranges from about 0.1% to about 1% by weight.

An additional active agent which may optionally be incorporated with Ala-Ile-Val into compositions of the present invention is a tripeptide having the sequence Serine-Leucine-Phenylalanine (Ser-Leu-Phe). Ser-Leu-Phe may be combined with Ala-Ile-Val in a weight ratio amount of from about 05:2 to about 2:05 Ser-Leu-Phe to Ala-Ile-Val, preferably from about 1 to about 1.

The peptide Serinylleucinylphenylalanine (Ser-Leu-Phe) is synthesized using FastMoc® chemistry (Applied Biosystems, Foster City, Calif.) on an ABI 430 A peptide synthesizer (Applied Biosystems). The peptide is synthesized on 0.25 mmol scale using 0.31 g fluorenylmethoxycabonyl-phenylalanine-p-benzyloxybenzyl alcohol resin (Fmoc-Phe-Wang resin) (0.8 mmol g-1), purchased from Advanced ChemTech (Louisville, Ky.) as the starting material. The peptide is synthesized utilizing the FastMoc® cycles, which include deprotection of the amino terminal Fmoc group with piperidine (Aldrich Chemical, Milwaukee, Wis.), 25% in N-methylpyrrollidinone (NMP) (J.T. Baker, Philipsburg, N.J.) and coupling of the next Fmoc-amino acid residue via activation of the carboxyl group with 0.45 M H-Benzotriazole-N,N,N',N'-Tetramethyluroniumhexafluorophosphate (HBTU) (Applied Biosystems).

The peptide is then cleaved from the resin by adding 9.5 ml Trifluroroacetic acid (TFA) mixed with 0.5 ml H20 to the peptidyl resin in a stoppered round bottom and allowed to stir for 1.5 hours at room temperature. The solution is then filtered through a medium porosity glass frit and the filtrate reduced in volume to 2 ml in vacuo. The solution was then diluted with 20 ml of $H_2O$ and washed three times with 20 ml of ether. The aqueous layer is lyophilized overnight.

The crude peptide is characterized using Ion Spray Mass Spectrometry (Sciex) and by reversed phase-high pressure liquid chromatography (RP-HPLC) using a Beckman HPLC system, 167 Detector, 126 Pumps (Beckman, Palo Alto, Calif.) with a gradient of 0%–40% $CH_3CN$ (0.1% TFA) over 40 min. on a Vydac (The Nest Group, Southborough, Mass.) column (4.6×250 mm, 5 pm 300Å) at a flow rate of 1 ml $min^{-1}$.

The crude peptide is then preparatively purified using RP-HPLC with the above conditions on a Vydac column (22×250 mm, 10 pm 300Å) at a flow rate of 10 ml $min^{-1}$.

COMPOSITIONS

Components of the topical, oral carrier are suitable for administration to the oral cavity of a human or other animal and are compatible with one another and the other components, especially the tripeptide(s), used in an oral composition of the present invention. The term "compatible" as used herein, means that the components are capable of being co-mingled with one another, in a manner such that there is no interaction which would substantially reduce the efficacy of the oral composition under ordinary use conditions. Preferred topical, oral carriers thus provide the desired characteristics for mouthwashes, mouth rinses, mouth sprays, dental treatment solutions, toothpastes, dental gels, toothpowders, prophylaxis pastes, lozenges, chewing gums, and the like. The topical, oral carriers of the present invention comprise components typically used in such compositions which are well known to a skilled practitioner. Such components include, but are not limited to, anticaries agents, antiplaque agents, anticalculus agents, dental abrasives, surfactants, flavoring agents, sweetening agents, binders, humectants, thickening agents, buffering agents, preservatives, coloring agents and pigments, ethanol and water.

Water is an optional component of the topical, oral carriers of the compositions of the present invention. Water employed in the preparation of the commercially suitable compositions should preferably be of low ion content and free of organic impurities. Water preferably comprises from about 2% to about 99%, more preferably from about 20% to about 95% of the compositions of the present invention. When in the form of toothpaste, the compositions preferably comprise from about 2% to about 45%, more preferably from about 30% to about 40%, water, while mouthwashes comprise preferably from about 45% to about 95%, more preferably from about 75% to about 90%, water.

Dental abrasives useful in the topical, oral carriers of the compositions of the present invention include many different materials. The material selected must be one which is compatible with the composition of interest and does not excessively abrade dentin. These include, for example, silicas, including gels and precipitates, calcium carbonate, dicalcium orthophosphate dihydrate, calcium pyrophosphate, tricalcium phosphate, calcium polymetaphosphate, insoluble sodium polymetaphosphate, hydrated alumina, and resinous abrasive materials such as particulate condensation products of urea and formaldehyde, and other materials such as those disclosed by Cooley et al. in U.S. Pat. No. 3,070,510, issued Dec. 25, 1962, incorporated herein by reference. Mixtures of abrasives may also be used.

Silica dental abrasives, of various types, can provide the unique benefits of exceptional dental cleaning and polishing performance without unduly abrading tooth enamel or dentin. For this reason they are preferred for use herein.

The silica abrasive polishing materials useful herein, as well as the other abrasives, generally have an average particle size ranging between about 0.1 and 30 microns, preferably between about 5 and 15 microns. The silica abrasive can be precipitated silica or silica gels such as the silica xerogels described in U.S. Pat. No. 3,538,230, issued Mar. 2, 1970 to Pader et al., and in U.S. Pat. No. 3,862,307, issued Jun. 21, 1975 to DiGiulio, both incorporated herein by reference. Preferred are the silica xerogels marketed under the tradename Syloid® by the W. R. Grace & Company, Davidson Chemical Division. Preferred precipitated silica materials include those marketed by the J. M. Huber Corporation under the tradename, Zeodent®, particularly the silica carrying the designation Zeodent 119®. These silica abrasives are described in U.S. Pat. No. 4,340,583, Wason, issued Jul. 20, 1982, incorporated herein by reference. Other suitable abrasives include alumina and the insoluble metaphosphates such as insoluble sodium metaphosphate (IMP).

Mixtures of abrasives may be used. The total amount of abrasive in the dentifrice embodiments of this invention can range from about 6% to about 70%, preferably from about 15% to about 50%, when the dentifrice is a toothpaste. Higher levels, as high as 90%, may be used if the composition is a tooth powder.

Flavoring agents can also be added to the oral compositions of the present invention to make them more palatable. Suitable flavoring agents include menthol, oil of wintergreen, oil of peppermint, oil of spearmint, oil of sassafras, and oil of clove. Flavoring agents are generally included in the subject compositions in amounts of from about 0% to about 3%, preferably from about 0.04% to about 2% by weight.

Coloring agents may be added to compositions of the present invention to improve appearance. If present, coloring agents typically are included at levels of from about 0.001% to about 0.5% by weight.

Sweetening agents are also preferred in the compositions of the present invention to make them more palatable. Sweetening agents which can be used include aspartame, acesulfame, saccharin salts, dextrose, levulose thaumatin, D-tryptophan, dihydrochalcones, and cyclamate salts. Saccharin salts are preferred. Sweetening agents are generally used in the subject compositions in amounts of from about 0% to about 6%, preferably from about 0.005% to about 5% by weight.

Oral compositions can also contain a surfactant. Suitable surfactants are those which are reasonably stable and form suds throughout a wide pH range, including nonsoap anionic, nonionic, cationic, zwitterionic and amphoteric organic synthetic detergents, and compatible mixtures thereof. Many of these suitable surfactants are disclosed in U.S. Pat. No. 4,051,234, issued to Gieske et al. on Sep. 27, 1977, and in U.S. Pat. No. 3,959,458 issued to Agricola, Briner, Granger and Widder on May 25, 1976, both of which are incorporated herein by reference. Surfactants are typically present in compositions of the present invention at a level of from 0% to about 10%, preferably from about 0.2% to about 4% by weight. Surfactants may also be used as solubilizing agents to help retain sparingly soluble components, e.g., some flavoring agents, in solutions. Surfactants suitable for this purpose include polysorbates and poloxamers.

In preparing oral compositions of the present invention, it is desirable to add binders and/or thickening agents, particularly to toothpaste compositions. Preferred binders and thickening agents include for example, carboxyvinyl polymers, polysaccharide gums such as xanthan gum, carrageenan, hydroxyethyl cellulose and water soluble salts of cellulose ethers such as sodium carboxymethyl cellulose and sodium carboxymethyl hydroxyethyl cellulose. Natural gums such as gum karaya, gum arabic, and gum tragacanth can also be used. Colloidal magnesium aluminum silicate or finely divided silica can be used as part of the thickening agent to further improve texture. These binders and thickening agents are generally present in the compositions of the present invention in amounts of from about 0% to about 6%, preferably from about 0.1% to about 5% by weight.

Another optional component of the oral carriers of the compositions of the present invention is a humectant. The humectant serves to keep toothpaste compositions from hardening upon exposure to air, and to give mouthwash and toothpaste compositions a moist feel to the mouth. Certain humectants can also impart desirable sweetness of flavor to mouthwash and toothpaste compositions. The humectant, on a pure humectant basis, generally comprises from about 0% to about 70%, preferably from about 2% to about 55%, by weight of the compositions herein. Suitable humectants for use in compositions of the present invention include edible polyhydric alcohols such as glycerin, sorbitol, xylitol, polyethylene glycol, and propylene glycol, especially sorbitol and glycerin.

Opacifiers may also be used in toothpastes of the present invention to render the toothpaste opaque. Suitable opacifiers include titanium dioxide and some abrasives including, for example, magnesium aluminum silicate. Opacifiers generally comprise from about 0% to about 4%, preferably from about 0.5% to about 3% by weight of the compositions herein.

Buffering agents are another optional component of the compositions of the present invention. Suitable buffering agents include any pharmaceutically-acceptable buffers safe for use within the oral cavity with low affinity for aluminum, gallium or indium. Examples of such agents include amino acids such as histidine and glycine, as well as ions of monocarboxylic acids such as acetate and benzoate. The buffering agents serve to retain the pH of the compositions within the preferred range. The amount of buffering agent desirable depends on buffering capacity of the particular agent. Generally the buffering agent comprises from about 0% to about 10%, preferably from about 0.2% to about 5%, by weight of the compositions herein.

Other optional components of the compositions of the present invention are preservatives. The preservatives prevent microbial growth in the compositions. Suitable preservatives include methylparaben, propylparaben, benzoates and ethanol. If the preservative is ethanol, it generally comprises from 0% to about 35% by weight, preferably from about 5% to about 15%, of the compositions herein. Other preservatives generally comprise from about 0% to about 5% by weight, preferably from about. 1% to about 2%, of the compositions herein.

Antimicrobial, antiplaque agents can also optionally be present in the oral compositions of the present invention, on the condition that they are compatible with the tripepride(s). Such agents may include, but are not limited to, triclosan, 2,4,4'-trichloro-2'-hydroxydiphenyl ether, as described The Merck Index, 11th Ed. (1989), p. 1520 (entry No. 9573); in U.S. Pat. No. 3,506,720; and in Eur. Pat. Appl. No. 0,251, 591 of Beecham Group, PLC, published Jan. 7, 1988, chlorhexidine, (Merck Index., No. 2090), alexidine (Merck Index, No. 222); hexetidine (Merck Index, No. 4624); sanguinarine (Merck Index, No. 8320); benzalkonium chloride (Merck Index, No. 1066); salicylanilide (Merck Index., No. 8299); domiphen bromide (Merck Index, No. 3411); cetylpyridinium chloride, (CPC) (Merck Index, No. 2024); tetradecylpyridinium chloride, (TPC); N-tetradecyl-4-ethylpyridinium chloride (TDEPC); octenidine; delmopinol, octapinol, and other piperidino derivatives; nicin preparations; zinc/stannous ion agents; antibiotics such as augmentin, amoxicillin, tetracycline, doxycycline, minocycline, and metronidazole; and peroxides, such as psylium peroxide, hydrogen peroxide, and magnesium monoperthalate and its analogs as described in U.S. Pat. No. 4,670,252; and analogs and salts of the above antimicrobial antiplaque agents. If present, the antimicrobial antiplaque agents may comprise from about 0% to about 6%, preferably from about 0.1% to about 5% by weight of the compositions of the present invention.

Nutrients can also be present in the oral composition of the present invention, on condition that they are compatible with the tripepride(s). Such agents may include folate, retinoids (Vitamin A), Vitamin C, Vitamin E and zinc. If present, the nutrients generally comprise from about 0.001% to about 10% by weight of the compositions of the present invention.

Other optional ingredients include a safe and effective amount of a fluoride ion source, which typically is in the form of a water-soluble fluoride compound. This water-soluble fluoride compound is typically present in the compositions of the present invention in an amount sufficient to give a fluoride concentration of from about 0.0025% to about 5.0% by weight, preferably from about 0.005% to about 2.0% by weight. Preferred fluoride sources are sodium fluoride, acidulated phosphate fluoride, and sodium monofluorophosphate. U.S. Pat. No. 3,678,154, issued Jul. 18, 1972 to Widder et al., the disclosure of which is incorporated herein by reference, discloses such salts as well as others.

Compositions of the present invention may also include one or more anticalculus agents, on the condition that they are compatible with the tripepride(s). Anticalculus agents which may be useful in the compositions of the present invention include diphosphonates such as 1-azocycloheptane-2,2-diphosphonate (AHP) and ethane-1-hydroxy-1,1-diphosphonate (EHDP), sodium zinc citrate, phosphocitrate, tripolyphosphate, and linear polycarboxylate (LPC); pyrophosphates or polyphosphates such as those disclosed in U.S. Pat. No. 4,590,066 issued to Parran & Sakkab on May 20, 1986 (e.g. tetrasodium pyrophosphate, tetrapotassium pyrophosphate, and dihydrogen disodium pyrophosphate); polyacrylates and other polycarboxylates such as those disclosed in U.S. Pat. No. 3,429,963 issued to Shedlovsky on Feb. 25, 1969 and U.S. Pat. No. 4,304,766 issued to Chang on Dec. 8, 1981; and U.S. Pat. No. 4,661,341 issued to Benedict & Sunberg on Apr. 28, 1987; polyepoxysuccinates such as those disclosed in U.S. Pat. No. 4,846,650 issued to Benedict, Bush & Sunberg on Jul. 11, 1989; nitrilotriacetic acid and related compounds as disclosed in U.S. Pat. No. 3,678,154 issued to Widder & Briner on Jul. 18, 1972; polyphosphonates as disclosed in U.S. Pat. No. 3,737,533 issued to Francis on Jun. 5, 1973, U.S. Pat. No. 3,988,443 issued to Ploger, Schmidt-Dunker & Gloxhuber on Oct. 26, 1976 and U.S. Pat. No. 4,877,603 issued to Degenhardt & Kozikowski on Oct. 31, 1989; all of these patents are incorporated herein by reference. If present, the anticalculus agents generally comprise from about 0.2% to about 13%, preferably from about 0.4% to about 6% of the compositions of the present invention. Preferred anticalculus agents are pyrophosphate.

Preferred compositions of the present invention are in the form of toothpastes. Components of such toothpastes generally include a dental abrasive (from about 10% to about 50%), a surfactant (from about 0.5% to about 10%), a thickening agent (from about 0.1% to about 5%), a humectant (from about 10% to about 55%), a flavoring agent (from about 0.04% to about 2%), a sweetening agent (from about 0.1% to about 3%), a coloring agent (from about 0.01% to about 0.5%) and water (from about 2% to about 45%). Such toothpastes may also include one or more of an anticaries agent (from about 0.05% to about 0.3% as fluoride ion), an anticalculus agent (from about 0.1% to about 13%), and an antiplaque agent (from about 0.1% to about 5%).

Other preferred compositions of the present invention are mouthwashes and mouthsprays. Components of such mouthwashes and mouthsprays include water (from about 45% to about 95%), ethanol (from about 0% to about 25%), a humectant (from about 0% to about 50%), a surfactant agent (from about 0.01% to about 7%), an flavoring agent (from about 0.04% to about 2%), a sweetening agent (from about 0.1% to about 3%), and a coloring agent (from about 0.001% to about 0.5%). Such mouthwashes and mouthsprays may also include one or more of an anticaries agent (from about 0.05% to about 0.3% as fluoride ion), an anticalculus agent (from about 0.1% to about 3%), and an antiplaque agent (from about 0.1% to about 5%).

Other preferred compositions of the present invention are dental solutions. Components of such dental solutions generally include water (from about 90% to about 99%), preservative (from about 0.01% to about 0.5%, thickening agent (from about 0% to about 5%), flavoring agent (from about 0.04% to about 2%), sweetening agent (from about 0.1% to about 3%), and surfactant (from 0% to about 5%).

Other preferred compositions may be non-aqueous mouthrinses. Suitable components are disclosed in U.S. Pat. No. 4,312,889 issued Jan. 26, 1982 to Melsheimer, and in U.S. Pat. No. 5,143,720 issued Sept. 1, 1992 to Lopes, both incorporated herein by reference. Alcohol free mouth rinses are also preferred. Suitable compositional components can are disclosed in U.S. Pat. No. 4,919,918, issued Apr. 24, 1990 to Cole et al., and in U.S. Pat. No. 5,283,056, issued Feb. 1, 1994 to Chung et al., and in PCT Appl. No. 9 401 081, published Jan. 20, 1990, each incorporated herein by reference.

Other embodiments of the oral compositions herein include lozenges. Suitable lozenge components (e.g. a candy base) are disclosed in U.S. Pat. No. 4,931,473, Jun. 5. 1990, to Kelleher et al. and in U.S. Pat. No. 4,139,627, Feb. 123, 1979 to Lane et al., both incorporated herein by reference.

Other preferred compositions include chewing gums. Chewing gum components (e.g. gum base, flavoring and sweetening agents) are disclosed in U.S. Pat. No. 4,083,955, Apr. 11, 1978 to Grabenstetter et al., the disclosure of which is incorporated herein by reference.

The pH of the subject compositions and/or its pH in the mouth can be any pH which is safe for the mouth's hard and soft tissues. Such pH's are generally from about 3 to about 10, more preferably from about 4 to about 8.

METHODS OF USE

Another aspect of the present invention involves methods for reducing or preventing dental plaque or gingivitis, by application of compositions comprising a safe and effective amount of Ala-Ile-Val, to tissues of the oral cavity. Such compositions are described hereinabove.

These methods involve administering a safe and effective amount of Ala-Ile-Val typically by administering an oral composition of the present invention, as described hereinabove to the oral cavity. Generally an amount of at least about 0.03 g to about 0.1 g of Ala-Ile-Val is effective. The teeth and other oral cavity tissues are "bathed" in the tripeptide.

When the oral composition is a toothpaste, typically from about 0.3 grams to about 15 grams, preferably from about 0.5 grams to about 5 grams, more preferably from about 1 to about 2 grams, of toothpaste is applied to an applicating device e.g., a toothbrush. The applicating device is then contacted with the oral cavity surfaces in a manner such that the oral composition is contacted with tissue of the oral cavity, especially the teeth and gums. The applicating device may be further used to effect an even distribution of the oral composition to the tooth surface, for example by brushing. The application preferably lasts for a period of from about 15 seconds to about 10 minutes, more preferably from about 1 minute to about 2 minutes. Following application, the toothpaste residue is typically removed from the tooth surface by using a liquid acceptable to the oral cavity, typically water, to rinse the oral cavity.

When the oral composition is a mouthwash, typically from about 1 mi. to about 20 mi., preferably from about 2 mi. to about 15 mi., most preferably from about 10 mi. to about 15 mi., of liquid mouthwash containing the antiplaque tripeptide(s) is introduced to the oral cavity. The liquid mouthwash is then agitated for from about 10 seconds to about 30 min., preferably from about 15 seconds to about 3 min., more preferably from about 30 seconds to about 2 minutes, within the oral cavity to obtain an improved distribution of the mouthwash over the tissue of the oral cavity. Following agitation, the mouthwash is typically expectorated from the oral cavity.

Application frequency is preferably from about once daily to about 4 times daily, more preferably from about 3 times weekly to about 3 times daily, more preferably still from about once to about twice daily for a dentifrice or liquid composition. A chewing gum or lozenge composition may be used from about once daily to about 5 times daily, more preferably from about 3 times weekly to about 4 times daily, more preferably still from about once to about three times daily. The period of such treatment typically ranges from about one day to a lifetime.

ORAL COMPOSITION EXAMPLES

The following non-limiting examples illustrate representative oral compositions containing active agents of the present invention. The compositions are made using conventional processes.

EXAMPLES I & II

The following representative examples of toothpaste compositions of the present invention are made by conventional processes by mixing the following:

| Component | Example I % by weight | Example II % by weight |
|---|---|---|
| Sorbitol | 42 | 35 |
| Saccharin Sodium | 0.13 | 0.2 |
| FD&C Blue (1% soln) | 0.05 | 0.05 |
| Precipitated Silica | 20 | 25 |
| Sodium Fluoride | — | 0.24 |
| Flavor | 0.9 | 1.5 |
| Sodium Alkyl Sulfate | 1 | 1.2 |
| Phosphoric Acid | 0.4 | — |
| Carbomer 940 | 0.25 | 0.25 |
| Xanthan Gum | 0.5 | 0.65 |
| Titanium Dioxide | 0.5 | 0.5 |
| Ala—Ile—Val | 0.05 | 0.1 |
| Ser—Leu—Phe | 0.05 | — |
| Purified Water | qs | qs |

EXAMPLE III

The following representative example of a mouth rinse composition of the present invention is made by conventional processes by mixing the following:

| Component | % by weight |
|---|---|
| Ala—Ile—Val | 0.1 |
| Ethanol | 12 |
| Glycerin | 10 |
| Dibasic Sodium Phosphate Heptahydrate | 0.07 |
| Saccharin Sodium | 0.08 |
| Monobasic Sodium Phosphate Monohydrate | 2.03 |
| Polysorbate 80 | 0.33 |
| FD&C Blue (1% Soln) | 0.02 |
| Flavor | 0.15 |
| Purified Water | qs |

EXAMPLE IV

The following representative example of a mouthwash composition of the present invention is made by conventional processes by mixing the following:

| Component | % by weight |
|---|---|
| Ala—Ile—Val | 0.15 |
| Flavor | 0.1 |
| Polysorbate 80 | 0.25 |
| Saccharin Sodium | 0.05 |
| Methylparaben | 0.2 |
| Propylparaben | 0.1 |

EXAMPLE V

The following representative example of a lozenge composition of the present invention can be made by conventional processes.

| Component | % by weight |
|---|---|
| Sorbitol | 90.5 |
| Hydroxypropyl Cellulose | 5 |
| Flavor | 2 |
| Mg Stearate | 1.5 |
| Ala—Ile—Val | 1 |
| Water | qs |

EXAMPLE VI

The following is a representative example of a chewing gum composition of the present invention. The chewing gum can be made by conventional processes.

| Component | % by weight |
|---|---|
| Gum Base | 20 |
| Plasticizer | 2 |
| Glycerin | 10 |
| Sweetener | 1 |
| Flavor | 1 |
| Ala—Ile—Val | 1 |
| Sorbitol powder | qs |

While particular embodiments of the present invention have been described, it will be obvious to those skilled in the art that various changes and modifications to the present invention can be made without departing from the spirit and scope of the invention. It is intended to cover, in the appended claims, all such modifications that are within the scope of the present invention.

What is claimed is:

1. A tripeptide having the amino acid sequence:
   Alanine-lsoleucine-Valine.
2. A method for inhibiting growth of dental plaque on tissues within an oral cavity of a human or other animals comprising topical administration, to tissues of such oral cavity, of a composition comprising a safe and effective amount of the tripeptide Alanine-lsoleucine-Valine.
3. The method of claim 2 for inhibiting growth of dental plaque on tooth surfaces within an oral cavity of a human or other animal comprising topical administration of the composition to tooth surfaces of such oral cavity.
4. The method of claim 2 wherein the composition comprises from about 0.01% to about 10% by weight of the tripepride.
5. The method of claim 2 wherein the composition comprises from about 0.01% to about 5% by weight of the tripeptide and from about 0.01% to about 5% by weight of a tripeptide having the amino acid sequence Serine-Leucine-Phenylalanine.

6. A dentifrice composition comprising:
(a) a safe and effective amount of the tripepride Alanine-Isoleucine-Valine; and
(b) a dentifrice carrier comprising a dental abrasive and a flavoring or sweetening agent.

7. The composition of claim 6 wherein the composition is a toothpaste comprising a surfactant, a humectant, and water.

8. The composition of claim 6 wherein the composition comprises a safe and effective amount of a fluoride anticaries agent.

9. The composition of claim 7 wherein the composition comprises a safe and effective amount of an anticalculus agent.

10. The composition of claim 7 wherein the composition comprises a safe and effective amount of an anticalculus agent and a fluoride anticaries agent.

11. The composition of claim 7 wherein the composition comprises a
safe and effective amount of an antimicrobial antiplaque agent.

12. The composition of claim 7 wherein the composition comprises a
safe and effective amount of a non-steroidal anti-inflammatory agent.

13. The composition of claim 7 wherein the composition comprises from
about 0.01% to about 10% by weight of the tripepride.

14. The composition of claim 7 wherein the composition comprises from about 0.01% to about 10% of the tripepride and from about 0.01% to about 10% by weight of a tripeptide having the amino acid sequence Serine-Leucine-Phenylalanine.

15. A mouthwash or mouth spray composition comprising:
(a) a safe and effective amount of the tripepride Alanine-Isoleucine-Valine; and
(b) a carrier comprising a flavoring or sweetening agent.

16. The composition of claim 15 wherein the composition is a solution comprising a surfactant.

17. The composition of claim 16 wherein the composition comprises a humectant and water.

18. The composition of claim 16 wherein the composition comprises ethanol.

19. The composition of claim 16 wherein the composition comprises a safe and effective amount of a fluoride anticaries agent.

20. The composition of claim 16 wherein the composition comprises a safe and effective amount of an antimicrobial antiplaque agent.

21. The composition of claim 16 wherein the composition comprises a safe and effective amount of a non-steroidal anti-inflammatory agent.

22. The composition of claim 16 wherein the composition comprises from about 0.01% to about 5% by weight of the tripepride.

23. The composition of claim 15 wherein the composition comprises from about 0.01% to about 10% by weight of the tripepride and from about 0.01% to about 10% by weight of a tripepride having the amino acid sequence Serine-Leucine-Phenylalanine.

* * * * *